United States Patent [19]
Lichtenhan et al.

[11] Patent Number: 5,939,576
[45] Date of Patent: Aug. 17, 1999

[54] METHOD OF FUNCTIONALIZING POLYCYCLIC SILICONES AND THE COMPOUNDS SO FORMED

[75] Inventors: Joseph D. Lichtenhan, Palmdale; Joseph J. Schwab, Lancaster; Frank J. Feher, Costa Mesa; Daravong Soulivong, Irvine, all of Calif.

[73] Assignee: The United States of America as represented by the Secretary of the Air Force, Washington, D.C.

[21] Appl. No.: 09/003,084

[22] Filed: Jan. 5, 1998

[51] Int. Cl.$^6$ .................................. C07F 7/08; C07F 7/10
[52] U.S. Cl. ..................... 556/460; 556/461; 556/459; 556/415; 556/419; 549/215; 540/487; 528/9; 528/10; 528/15; 528/19
[58] Field of Search ..................... 556/460, 461, 556/459, 415, 419; 549/215; 540/487; 528/9, 10, 15, 19

[56] References Cited

U.S. PATENT DOCUMENTS

| 5,484,867 | 1/1996 | Lichtenhan et al. | 556/460 X |
| 5,589,562 | 12/1996 | Lichtenhan et al. | 556/460 X |

*Primary Examiner*—Paul F. Shaver
*Attorney, Agent, or Firm*—Thomas C. Stover

[57] ABSTRACT

A synthetic process for the selective preparation of reactive polyhedral oligomeric silsesquioxanes (POSS) as well as polyhedral oligomeric silicate (POS) (spherosilicate) is provided. The inventive process employs the use of metal catalyzed hydrosilylation reactions for the selective reaction of silane containing polyhedral oligomeric silsesquioxanes or silicates with olefinic reagents bearing functionalities useful for grafting reactions, polymerization chemistry and sol-gel processes. The invention also discloses metal-catalyzed hydrosulfidation reactions and metal-catalyzed hydrophosphidation reacttions for functionalization of polycyclic silicones.

18 Claims, No Drawings

METHOD OF FUNCTIONALIZING POLYCYCLIC SILICONES AND THE COMPOUNDS SO FORMED

STATEMENT OF GOVERNMENT INTEREST

The invention described herein may be manufactured and used by or for the Government for governmental purposes without the payment of any royalty thereon.

FIELD OF THE INVENTION

This invention relates to a method of functionalizing polycyclic silicones particularly when employing catalysts promoting oxidative addition and the resulting compounds.

BACKGROUND OF THE INVENTION

Polyhedral oligomeric silsesquioxane (POSS) cage molecules and polyhedral oligomeric silicate (POS) (spherosilicate) cage molecules or reagents are increasingly being utilized as building blocks for the preparation of novel catalytic materials and as performance enhancement additives for commodity and engineering polymers. The physical sizes and structures of POSS and POS reagents are on the nanometer dimension ($10^{-9}$m) and they can be described as the smallest "silica-like" particles possible. Their nanometer size and unique hybrid (inorganic-organic) chemical composition are responsible for the many desirable property enhancements which have been observed upon incorporation of POSS/POS reagents into polymer systems. The most attractive POSS building blocks for the synthesis of linear polymer systems are POSS reagents that posses only one or two reactive chemical functionalities. When incorporated into a polymerization reaction these reagents provide high yields of linear polymers which are essentially free from impurities and have controllable properties through the appropriate selection of synthesis processes and/or starting materials. Conversely, the most attractive POSS building blocks for the synthesis of network polymers and/or use in sol-gel processes are POSS reagents which have been appropriately funtionalized with groups containing three or more reactive functionalities.

Three primary synthetic routes to functionalized POSS and POS based cage reagents have been reported. These have involved the following: (1) Polycondensation of trifunctional $RSiY_3$ precursors where R=a hydrocarbon and Y is a hydrolizable functionality such as chloride, an alkoxide or silanol. (2) Functionalization of fully substituted silane compounds such as via hydrosilylation or chlorination chemistry. Similarly, silylation of anionic species has been reported to produce functionalized species. Wiedner, et al U.S. Pat. No. 5,047,492, teach the production of exhaustively functionalized polyhedral oligomeric silsesquioxanes through processes involving either the addition of hydrogen atoms bonded directly to silicon atoms onto aliphaticly unsaturated compounds or the addition of sulfur atoms onto aliphaticly unsaturated compounds. Laine et al, Macromolecules, (1996), v. 29:2327–2330, also teach the addition of hydrogen atoms bonded directly to silicon atoms onto aliphaticly unsaturated compounds to produce polyfunctional silsesquioxanes.

Without exception, all of the reported methods have limited utility because they suffer from one or more of the following draw backs. (1) The synthetic route does not afford significant stereochemical control over the placement of the functionality on the cage species. (2) The method does not afford control over the degree of substitution that can take place and results in the formation of isomeric mixtures. (3) The type of organic functionality that can be incorporated on the cage is limited because the methods are intolerant to a broad range of chemical functionalities. (4) The methods do not afford a high yield route to the desired product, which results in the formation of impurities arising from side reactions that must be subsequently removed. (5) The functionalities are limited to the addition of hydrogen atoms bonded directly to heteroatoms (i.e. silicon or sulfur).

In the prior art is a reference to preparation of POSS monomers and synthesis of polymers therefrom, U.S. Pat. No. 5,484,867 to J. D. Lichtenhan et al (1996), which reference, however, is not believed to suggest the present invention.

Accordingly, there is need and market for improved functionalization of polycyclic silicones that overcomes the above prior art shortcomings.

There has now been developed, per the invention, efficient methods for the selective functionalization of the above polyfunctional species using the novel process steps discussed below.

SUMMARY OF THE INVENTION

Broadly the present invention provides a method for the functionalization of polycyclic silicones (PS) comprising, contacting a solution of formula 2 (shown below) with effective amounts of olefins of alkyls, cyclics, aryls, siloxys or isomers thereof containing R4 (defined below), in the presence of effective amounts of a catalyst which promotes oxidative addition to produce a product of formula 4 (shown below).

The invention also provides the above product of formula 4.

That is, the present invention teaches the functionalization of POSS and POS species through (1) transition metal catalyzed reactions which employ catalysts which promote oxidative addition, eg. hydrosilylation catalysts, as claimed in the present application and (2) transition metal catalyzed metathesis as claimed in a companion patent application filed herewith, entitled "METHOD OF FUNCTIONALIZING POLYCYCLIC SILICONES AND THE RESULTING COMPOUNDS" by the same inventors. Both functionalization methods employ olefinic reagents bearing chemical functionalities useful for grafting reactions, polymerization chemistry and sol-gel processes.

DESCRIPTION OF PREFERRED EMBODIMENTS

As noted above, two inventive chemical derivitization methods have been developed for the functionalization of POSS and POS reagents. Each method utilizes a transition metal-based catalyst to selectively transform organic substituents on polyhedral oligomeric silsesquioxane molecules into reactive chemical functionalities that are more desirable for grafting reactions, polymerizations, sol-gel processes and catalysis chemistry.

While the present application describes both of the above methods, the emphasis herein is on catalysts which promote oxidative addition, as noted above.

Definitions:

By "catalysts which promote oxidative addition" as used herein, is meant, catalysts which promote a hydrosilylation reaction, a hydrosulfonation reaction and/or a phosphorylation reaction.

The primary action of the metathesis transformation is to exchange functionalities between olefinic hydrocarbons (shown below). A similiar process described as acyclic diene metathesis polymerizations or ADMET, uses the same catalysts, and can be used to polymerize appropriately functionalized POSS and POS reagents with dienes.

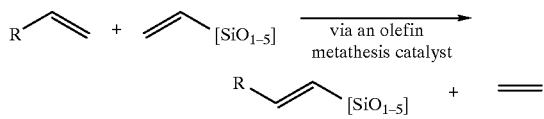

where R is $CH_3$ or H.

Example of olefin metathesis.

The use of metathesis catalysts to selectively manipulate the chemical functionality contained on polyhedral oligomeric silsesquioxanes and related molecules including spherosilicates had not been demonstrated prior to the present invention. Metathesis reactions can be carried out on POSS and POS systems when POSS/POS molecules bear olefinic substituents and preferably when the reactions are conducted in dilute solutions (See Rx.1&2, below, transformation of formula 1 into formula 2 & formula 3 into formula 4).

where

in 1–8 instances and R in 7–0 instances, And where R=—CH=$CH_2$ (vinyl), —$CH_2$CH=$CH_2$ (allyl), —$CH_2$($CH_2$)$_n$CH=$CH_2$ (α-olefins, n=1–42), —OSi(Me)$_2$$CH_2$($CH_2$)$_n$CH=$CH_2$ (α-olefins, n=1–42), —($CH_2$)$_n$CH=CH($CH_2$)$_n$$CH_3$ (cis and trans internal olefins, n=1–42), —OSi(Me)$_2$($CH_2$)$_n$CH=CH($CH_2$)$_n$$CH_3$ (cis and trans internal olefins, n=1–42), —Si($CH_3$)$_2$CH=$CH_2$ (dimethylvinylsilane), —Si($CH_3$)$_2$$CH_2$CH=$CH_2$ (dimethylallylsilane), —OSi($CH_3$)$_2$CH=$CH_2$ (dimethylvinylsiloxane), —OSi($CH_3$)$_2$$CH_2$CH=$CH_2$ (dimethylallylsiloxane), cyclic olefins including the following:

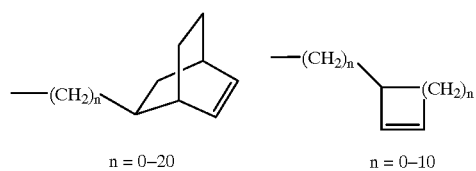

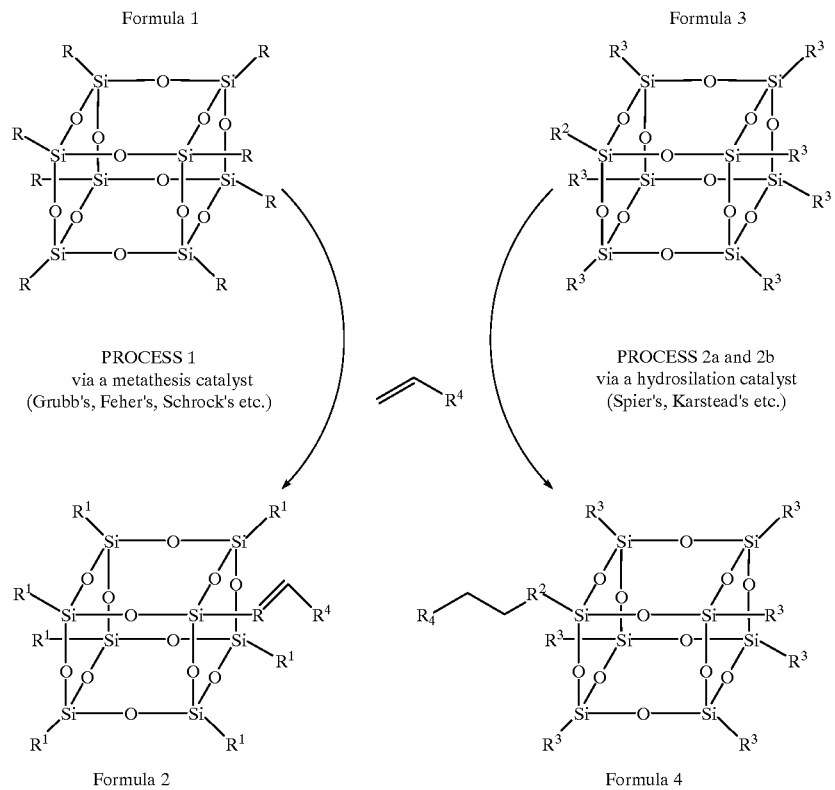

Rx. 1 Functionalization of POSS via metathesis & Rx.2 via hydrosilylation.
Formula 4 is mono-substituted as indicated.

—OSi(Me)₂(CH₂)ₙ— 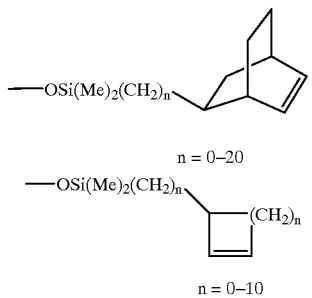

n = 0–20

—OSi(Me)₂(CH₂)ₙ—(CH₂)ₙ n = 0–10 where II R²=—H (hydrido) III R²=—Si(CH₃)₂H (dimethylsilane), —OSi(CH₃)₂H (dimethylhydridosiloxane), —OSi(CH₃)₂(CH₂)ₙSi(CH₃)₂H, —OSi(CH₃)₂(CH₂)ₙOSi(CH₃)₂H, —OSi(CH₃)₂(OSi(CH₃)₂O)ₙSi(CH₃)₂H, —OSi(CH₃)₂(CH₂)ₙ(C₆H₆)ₙ(CH₂)ₙSi(CH₃)₂H, —OSi(CH₃)₂(CH₂)ₙ(C₆H₆)ₙSi(CH₃)₂H, —OSi(CH₃)₂(CH₂)ₙ(C₆H₆)ₙOSi(CH₃)₂H, —(CH₂)ₙOSi(Me)₂H, —O(CH₂)ₙOSi(Me)₂H, —O(CH₂)ₙSi(CH₃)₂H, —(CH₂)ₙ(C₆H₅)ₙOSi(Me)₂H, —O(CH₂)ₙ(C₆H₅)ₙOSi(Me)₂H, —(CH₂)ₙ(C₆H₅)ₙSi(Me)₂H, and n=1–42, IV R²=—(CH₂)ₙSH (alkylsulfide), —(CH₂)ₙPH₂ (alkylphosphine), —(CH₂)ₙP(R)H (dialkyl-phosphine), and n=1–42, V R³=R and can include hydrocarbon radicals such as —CH₃ (methyl), —CH₂CH₃ (ethyl) and their higher analogues such as —CH₂(CH₂)ₙCH₃ as well as branched isomers and cyclic isomers including cyclo-C₅H₉ (cyclopentyl), cyclo-C₆H₁₁ (cyclohexyl) and aromatic analogues —C₆H₅ (phenyl), and n=1–42 and VI R⁴=all organic functionalities commonly used in polymerizations, grafting reactions and sol-gel processes to include: epoxides, caprolactams, cyclicolefin, α-olefins, fluorinated α-olefins and the like, mono, di and tri-halides, (eg. 5-bromo-1-pentene) alcohols, acids, esters, amines, nitriles, cyanates, amides, alcohols, silanols, trihalosilanes, trialkoxysilanes and the like.

Alternatively R⁴ can also contain cis or trans internal olefins such as but not limited to the following formulas: CH₃(CH₂)ₙCH=CH(CH₂)ₙR⁴ (n=0–42) and (CHF)n—CF₃, —(CH₂)ₙ—CF₃ (n=0–42).

Although all of the above chemistry has been depicted using fully condensed T₈ type Si—O frameworks (eg. where T₈=Si₈O₁₂), a logical extension of this chemistry to other frameworks can be envisioned including T₁₀=Si₁₀O₁₅ & T₁₂=Si₁₂O₁₈ and the like. In other examples, olefins and silanes on structures including the following, can be prepared:

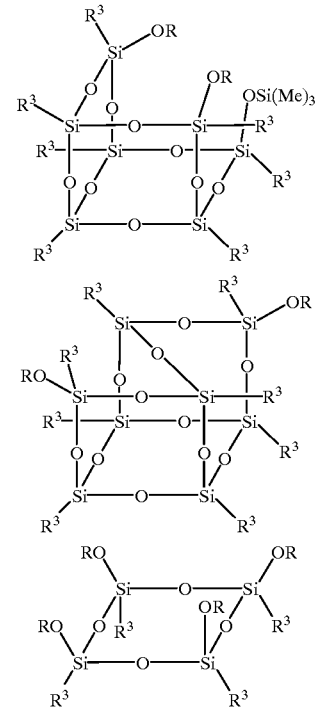

The metathesis process can also be utilized to graft and polymerize POSS/POS reagents into linear as well as crosslinked polymeric systems. The process requires that POSS/POS systems contain olefinic functionalities that are long enough to allow the cages to become polymerized. For example (vinyl)₈T₈ cannot be self polymerized through metathesis because the vinyl group is not of sufficient length to permit the process to occur, however, the compounds (vinylMe₂SiO)₈T₈ and (allyl)₈T₈ can be self polymerized using metal catalyzed metathesis (Rx. 3). Furthermore, this methodology can be extended to include ring closing metathesis of the olefins across the face of a T₈ (Si—O) framework to give macrocyclic rings.

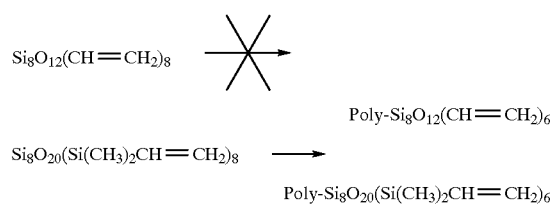

Rx. 3 Examples of self polymerization via olefin metathesis.

The use of metathesis chemistry in polymerization and grafting reactions with organic reagents has been in part described. The use of metathesis catalysts to incorporate POSS/POS reagents into existing polymer systems has not been described, but has been considered in order to improve the thermal properties (improved flame resistance, increased glass transition, increased melt viscosity) of olefin-bearing polymers such as EPDM, PP, PE, Pb and siloxanes.

Transformations by hydrosilylation are readily conducted using a variety of catalysts which have in part been previously described The primary action of the hydrosilylation transformation is to saturate the olefinic functionalities through the addition of a silicon-hydrogen bond across the olefinic carbons (Rx.4). The hydrosilylation process can be carried out on both alkenes (vinylic) and alkynyl (acetylenic) olefins. In addition to the use of transition metal-based catalysts the reaction can be catalyzed through the aid of radicals. Related processes involving the addition of sulfur-hydride (S—H) and phosphorous-hydride (P—H) bonds across olefins are also known to occur and can also be catalyzed with radical sources such as (organoperoxides such as the Lupersol™ derivatives, and organic azo compounds such as azobisisobutyronitrile (AIBN)).

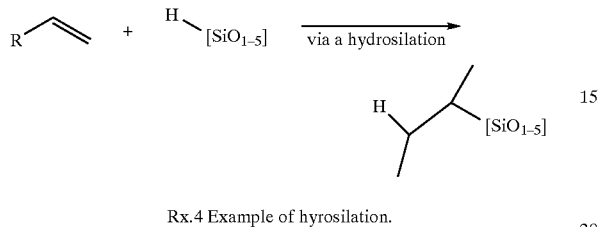

Rx.4 Example of hyrosilation.

The hydrosilylation process taught in this disclosure utilizes the same functionalized olefinic feedstocks that are preferred for use in functionalizations via cross-metathesis. The primary difference between the two processes being that the final POSS/POS product from hydrosilylation does not contain an olefin in the linkage from the POSS/POS cage to the new functionality. (See Rx. 2, transformation of formula 3 into formula 4). It has been found that in practice many olefins do not readily undergo hydrosilylation to compounds such as formula 3 where $R^2$=H (Rx.5). Apparently, as in the case of olefin self metathesis, the silane functionality must have the correct length in order to undergo clean hydrosilylation with some olefins.

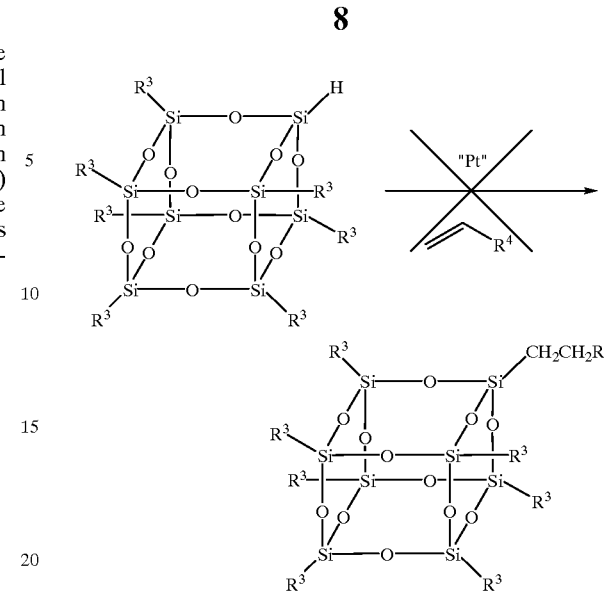

Rx.5 Hydrosilylation of some olefins fails (Prior Art).

In these cases, where the hydrosilylation is slow or fails, extension of the silane functionality with radicals described for group III provides polyhedral oligomeric silsesquioxanes which undergo clean hydrosilylation. (Rx.6). This process represents a key synthetic route to POSS reagents containing only one or two reactive functionalities.

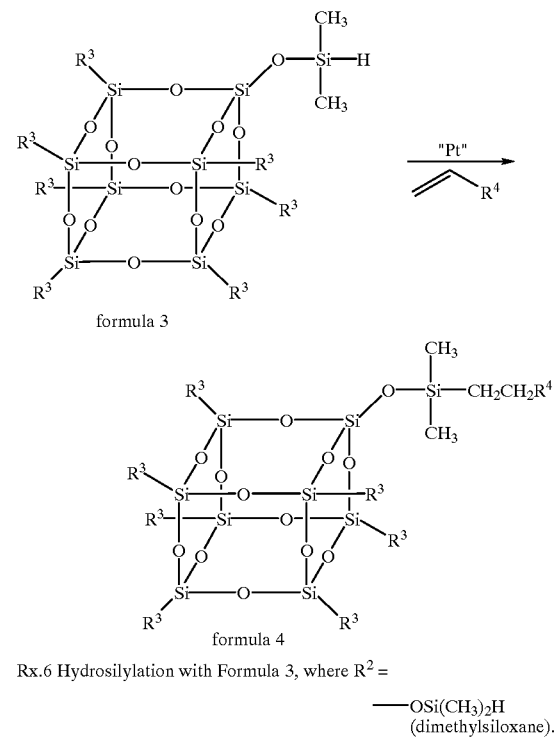

Rx.6 Hydrosilylation with Formula 3, where $R^2$ =

—OSi(CH$_3$)$_2$H
(dimethylsiloxane).

Compounds of this type are based on the silanol, shown in Rx.7, which is easily prepared from the silyl chloride. This silanol is unique in that it does not undergo self condensation upon hydrolysis. The silanol is cleanly con verted to a variety of silanes of the type described for group III, via reaction with the appropriate silylating agent (Rx.8).

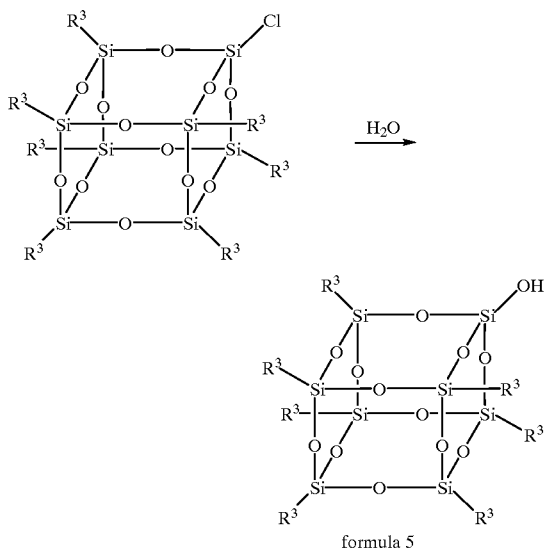

Rx.7 Synthesis of a key polyhedral oligomeric silanol.

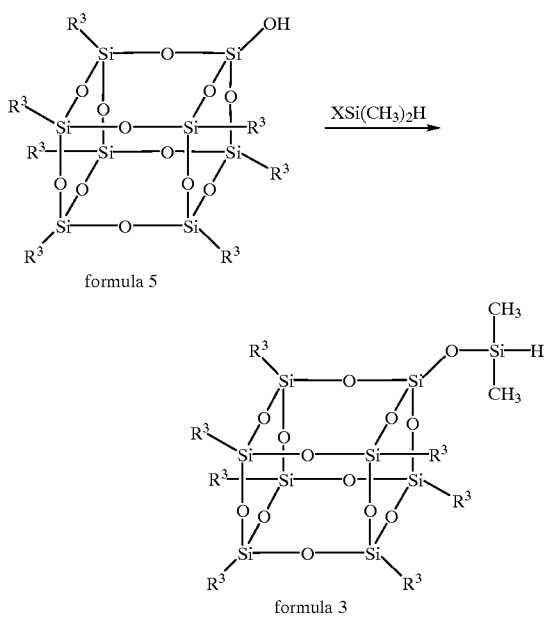

Rx.8 Conversion of silanol into silane. where X = halogen, NR$_2$, N(Ph)CON(c-C$_4$H$_8$).

Use of Invention

Use of the processes taught herein cover three fundamental areas: 1) The synthesis of POSS and/or POS monomers containing graftable or polymerizable functionality. 2) The use of POSS and/or POS monomers containing graftable or polymerizable funtionality in the synthesis of linear polymer systems. 3) The use of POSS and/or POS monomers in the synthesis of network polymers particularly via crosslinking of reactive functionalities either by olefin metathesis chemistry or by sol-gel processes.

The methodology taught in this application can be used to prepare a wide range of POSS and/or POS monomers via olefin metathesis or hydrosilylation chemistries. Monomers containing anywhere from one to eight reactive functionalities suitable for grafting and/or polymerization can be prepared. The invention also teaches the synthesis of new POSS monomers suitable for use in in hydrosilation chemistry. In particular the synthesis of POSS silanes from stable, monofuntional silanols. These new silanes have been shown to participate in hydrosilation reactions where previously known silanes have failed.

The monomers, particularly those containing only one or two graftable and/or polymerizable groups, prepared by the methodology described in this disclosure can be used to prepare taractable, linear polymer systems. Furthermore, the methodology, particularly the olefin metathesis chemistry and/or ADMET, can be used to prepare linear, tractable polymers and/or oligomers directly from POSS and/or POS monomers bearing olefin substituents.

The monomers, particularly those containing more than two graftable and/or polymerizable groups, prepared by the methodology described in this disclosure can be used to prepare network polymer systems. Network polymers can be formed directly from appropriately functionalized POSS and/or POS monomers using sol-gel techniques. The methodology, particularly the olefin metathesis chemistry and/or ADMET, can be used to prepare network polymers directly from POSS and/or POS monomers bearing olefin substituents. Finally the POSS/POS reagents containing olefinic or hydridic functionalities can also be utilized to prepare network polymers using established vulcanization processes.

Further discription re the inventive processes:

In accordance with one aspect of the present invention, compounds of the formula 2 or 4 (in which R is at least in part, a radical of formulas described previously for (I) and R$^2$ is at least in part, a radical having formulas previously described for (III)) can be prepared by reacting compounds of the formula 1 or 3, respectively, as indicated in Rx.1 & Rx.2 above, with, eg. radicals having the formulas previously described for (V).

If Rx.1 is employed, R can represent a radical of formula (I) (and proceed as "process 1", described below) and the process is preferably carried out in the presence of an olefin metathesis catalyst and/or compounds thereof.

If Rx.2 is employed, R$^2$ can represent a radical of formula (III) (and proceed as "process 2a", described below) and the process is preferably carried out in the presence of platinum metals and/or compounds thereof.

Also, if Rx.2 is employed, R$^2$ can represent a radical of formula (III) (and proceed as "process 2b", described below) and the process is preferably carried out in the presence of free radicals, in particular in the presence of organic peroxides, azo compounds and/or under irradiation with high energy electromagnetic radiation, such as UV light.

Process 1; functionalization via metathesis;

Preferred metathesis catalysts include molybdenum, tungsten, rhenium and ruthenium metals and/or alloys thereof, mixtures and/or chemical compounds thereof. Homogeneous catalyst systems are particularly preferred. All of the catalysts which have been or could have been employed heretofore for the metathesis of both internal and terminal olefins can be employed here. Examples of such catalysts are metallic and finely divided metals on supports such as silicon dioxide and/or aluminum oxide, all compounds of molybdenum, tungsten, rhenium and ruthenium containing alkylidene and/or alkykidyne ligands including the halides, alkoxides and siloxides of such compounds.

The metathesis catalyst is preferably employed in amounts from 0.1 to 30% by weight of catalyst to POSS/POS, in particular <1% by weight. Process 1 is preferably carried out at temperatures from 0° C. to 50° C., in particular from 22° C. to 25° C. The process can be carried out under the pressure of the surrounding atmosphere, that is for example 760 mm Hg (torr), and it can also be carried out under higher or lower pressures. Pressures from 1 torr to 760 torr in particular less than 700 torr are preferred. The process can also be carried out with the aid of a purge gas such as air or nitrogen. Flow rates from 10 ml/min to 10 liters/min or greater can be used, with rates of 10–50 ml/min being preferred.

Process 2a, functionalization via hydrosilaton;

Preferred platinum metals and/or compounds thereof include platinum, palladium, rhodium and iridium, alloys and chemical compounds thereof and mixtures thereof. All of the catalysts which have been or could have been employed heretofore for the hydrosilylation of hydrogen atoms to olefins can be employed here. Examples of such catalysts include Speier's and Karstead's catalysts.

The hydrosilylation catalyst is preferably employed in amounts from 0.5% to 30% by weight, in particular 1% to 5% by weight. Process 1 is preferably carried out at temperatures from 20° C. to 150° C., in particular from 50° C. to 120° C. The process can be carried out under the pressure of the surrounding atmosphere, that is for example 760 mm Hg, and it can also be carried out under higher or lower pressures. Pressures from 0.01 torr to 760 torr in particular 100 to 1000 torr are preferred. The process can also be carried out with the aid of a purge gas such as air or oxygen. Flow rates from 10 ml/min to 10 liters/min or greater can be used, with rates of 10–50 ml/min being preferred.

Process 2b; functionalization via radicals;

Preferred free radical sources include peroxides, particularly organic peroxides, and azo compounds eg. azobisisobutyronitrile (AIBN). All of the free radical sources which have been or could have been employed heretofore for the free radical addition of sulfur or phosphorous centers to olefins can be employed here.

The free radical source is preferably employed in amounts from 0.01% to 5% by molar weight, in particular 0.1% to 1% molar by weight. Process 1 is preferably carried out at temperatures from 20° C. to 150° C., in particular from 50° C. to 120° C. The process can be carried out under the pressure of the surrounding atmosphere, that is for example, 760 mm Hg, and it can also be carried out under higher or lower pressures. Pressures from 0.01 torr to 1000 torr or higher in particular 760 to 800 torr are preferred.

Precursor preparation for Processes 2a & 2b;

Compounds of formula 3 in which $R^3$ is at least in part a radical of formulas described previously for (V) and $R^2$ is at least in part a radical having formulas previously described for (III), can be prepared by reacting compounds of the formula

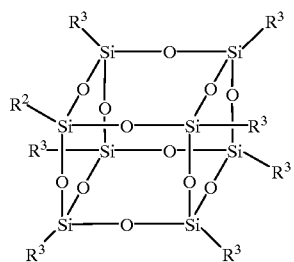

formula 3 with radicals having the formulas previously described for (V).

Compounds of formula 3 in which $R^3$ is at least in part a radical of formulas described previously for (V) and $R^2$ is at least in part a radical having formulas previously described for (III), can be prepared by reacting compounds of the formula

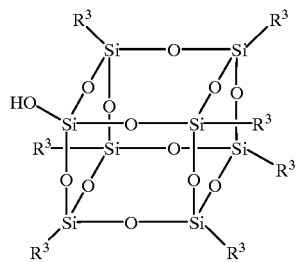

formula 5 with radicals having the formulas previously described for (III).

The following examples are intended to illustrate the present invention and should not be construed in limitation thereof.

Example 1

Hydrogenation of $Si_8O_{12}(CH=CHCH_2CH_2CH_3)_8$.

The $Si_8O_{12}(CH=CHCH_2CH_2CH_3)_8$ silsesquioxanes (19 mg), catalyst (7 mg of 10% Pd/C), and ethyl acetate (2 mL) were placed in the Parr reactor. After purging three times with $H_2$ (pressurizing to 400 psi and venting), the reactor was charged with $H_2$ (160 psi) and stirring at room temperature for 50 hours. The catalyst was removed by filtration through a short column of silica gel and washed with methylene chloride. Rotary evaporation of the filtrate quantitatively gave a colorless oil. The product was octapentyloctasilsesquioxane, $Si_8O_{12}((CH_2)_4CH_3)_8$ (or $R^3_8T_8$), an example of formula 4.

$^1$H NMR (500 MHz, $C_6D_6$, 25° C.): δ 1.69–1.63 (m, 16 H, $CH_2$), 1.40–1.27 (m, 32H, $CH_2$), 0.88 (t, 40 H, $SiCH_2$ and $CH_3$, $^3J_{H-H}$=7.3 Hz). $^{13}C\{^1H\}$ NMR (75 MHz, $C_6D_6$, 25° C.): δ 35.08 ($CH_2$), 22.84 ($CH_2$), 22.49 ($CH_2$), 14.12 ($CH_3$), 12.55 ($SiCH_2$). $^{29}Si\{^1H\}$ NMR (99 MHz, $C_6D_6$, 25° C.): δ −68.2.

Example 2

Reaction of $R_7T_7(OH)_3$ with tetrachlorosilane and water.

Tetrachlorosilane (2.59 mL, 3.84 g, 22.6 mmol, 1.1 eq) in diethyl ether (10 mL) was added to a solution of POSS trisilanol, $R_7T_7(OH)_3$, (R=cyclohexyl) (20.00 g, 20.54 mmol) and triethylamine (42.9 mmol, 31.8 g, 308 mmol, 15 eq) in diethyl ether (700 mL). An immediate precipitate of triethylamine hydrochloride formed and the reaction mixture was stirred for 72 h. After this time the reaction mixture was transferred to a sepratory funnel and washed with successive portions of water (2×150 mL), 1M hydrochloric acid (2×150 mL), water (150 mL) and saturated sodium chloride (150 mL). The reaction mixture was allowed to stand over water for 18 h. The water was removed and the diethyl ether layer dried over anhydrous magnesium sulfate. Removal of the diethyl ether provided 20.51 g (98% of theory) of $R_7T_8(OH)$ as a white microcrystalline solid. The product was hepatcyclohexyloctasilsesquioxane silanol, (c—$C_6H_{11}$)$_7Si_8O_{12}$(OH) (or $R_7T_8(OH)_1$),. This is a new chemical compound and a precursor to formula 3.

$^1$H NMR (300.135 MHz, CDCI$_3$, 305° K) δ 2.36 (s, 1 H, Si—OH), 1.73 (m, 35 H,CH$_2$), 1.25 (m, 35 H, CH$_2$), 0.79 (m, 7 H, CH). $^{13}$C NMR (75.475 MHz, CDCI$_3$, 305° K) δ 27.46, 26.88, 26.62, 26.56 (for CH$_2$), 23.18, 23.11, 23.01 (for CH). $^{29}$Si NMR (59.624 MHz, CDCI$_3$, 305° K) δ-67.77, -68.54, -99.

For R=cyclopentyl the reaction was carried out under exactly the same conditions to provide $R_7T_8(OH)$ in 99% experimental yield. The product was hepatcyclopentyloctasilsesquioxane silanol, (c—$C_5H_9$)$_7Si_8O_{12}$(OH) (or $R_7T_8(OH)_1$). This is a new chemical compound (formula 5) and a precursor to formula 3.

$^1$H NMR (300.135 MHz, CDCI$_3$, 305° K) δ 2.42 (s, 1 H, Si—OH), 1.76 (m, 14 H, for cyclopentyl CH$_2$), 1.50 (m, 42 H, for cyclopentyl CH$_2$), 1.02 (m, 7 H, for cyclopentyl CH). $^{13}$C NMR (75.475 MHz, CDCI$_3$, 305° K) δ (27.31, 26.02, 26.96 for cyclopentyl CH$_2$), (22.26, 22.20, 22.12 for cyclopentyl CH). $^{29}$Si NMR (59.624 MHz, CDCI$_3$, 305° K) δ-65.63, -66.24 (3:4), -99.95.

Example 3

Reaction of $R_7T_8(OH)$ with dimethylchlorosilane.

A solution of dimethylchlorosilane (1.8 mL, 1.5 g, 16.2 mmol, 1.1 eq) in tetrahydrofuran (5 mL) was added to a solution of $R_7T_8(OH)$, (R=cyclohexyl) (15 g, 14.8 mmol) and triethylamine (6.2 mL, 4.5 g, 44.3 mmol, 3 eq) in tetrahydrofuran (35 mL). An immediate precipitate of triethylamine hydrochloride formed and the reaction mixture was stirred for 72 h. After this time the reaction mixture was transferred to a sepratory funnel and washed with successive portions of water (2×100 mL), 1M hydrochloric acid (2×100 mL), water (100 mL) and saturated sodium chloride (100 mL). The tetrahyrofuran solution was dried over anhydrous magnesium sulfate. Removal of the tetrahydrofuran provided 15.82 g ( 99% of theory) of $R_7T_8OSi(Me_2)H$ as a microcrystalline solid. The product was dimethylsilyl hepatcyclohexyloctasilsesquioxane (or $R_7T_8(OSiR^3_2H)_1$) or (c—$C_6H_{11}$)$_7Si_8O_{12}$(OSi(CH$_3$)$_2$H). This is a new chemical compound and an example of formula 3.

$^1$H NMR (300.135 MHz, CDCI$_3$, 305° K) δ 4.74 (sept, 1 H), Si—H, 1.74 (m, 35 H,CH$_2$), 1.25 (m, 35 H, CH$_2$), 0.77 (m, 7 H, CH), 0.25 (d, 6 H, Si—CH$_3$). $^{13}$C NMR (75.475 MHz, CDCI$_3$, 305° K) δ 27.50, 26.91, 26.67, 26.57 (for CH$_2$), 23.16, 23.07 (for CH), 0.27 (Si—CH$_3$). $^{29}$Si NMR (59.624 MHz, CDCI$_3$, 305° K) δ-2.97, -67.92, -68.96, -68.6, -107.6.

Example 4

Reaction of $R_7T_8OSi(Me_2)H$ with diallylbisphenol A (#3→#4).

A 0.05 mL portion of hydrosilylation catalyst (a solution of platinum-olefin complex in toluene) was added to a solution of $R_7T_8OSi(Me_2)H$, (R=cyclohexyl) (11.0 g, 10.2 mmol, 1eq) and diallylbisphenol A (12.6 g, 41 mmol, 4eq) in tetrahydrofuran (110 mL) contained in a thick walled glass reaction vessel. The reaction mixture was heated to 70° C. for 72 h. After this time the tetrahydrofuran solvent was removed to give a viscous, semisolid residue. Extraction of the residue with acetonitrile gave a white solid which was collected by vacuum filtration and dried to provide 13.6 g (96% of theory) of the mono-POSS bisphenol A as a pale yellow solid. The product was mono-allyl, mono-dimethylsiloxypropyl hepatcyclohexyloctasilsesquioxane bisphenol A (or monoPOSS-monoallyl-bisphenol A) (or $R^3_7T_8(R^2-R^4)_1$) or CH$_2$=CHCH$_2$(HO)C$_6$H$_3$C(CH$_3$)$_2$C$_6$H$_3$(OH)(CH$_2$)$_3$Si(CH$_3$)$_2$OSi$_8$O$_{12}$(c—C$_6$H$_{11}$)$_7$. This is a new chemical compound and an example of formula 4 (#4).

$^{13}$C NMR (75.475 MHz, CDCI$_3$, 305° K) δ 151.89, 151.37, 143.59, 143.11, 136.67, 128.73, 128.64, 127.45, 126.31, 125.44, 124.35, 116.21, 115.26, 114.69, 41.70, 35.50, 33.78, 31.19, (27.50, 27.44, 26.91, 26.86, 26.67, 26.57 for cyclohexyl CH$_2$), 23.64, (23.16, 23.08 for cyclohexyl CH), 17.69, 0.19. $^{29}$Si NMR (59.624 MHz, CDCI$_3$, 305° K) δ 11.39, -67.96, -68.53 (3:4), -108.2.

As can be seen, Applicants' inventive methods enable the rapid and high yield preparation of functionalized POSS/POS reagents for use in a variety of chemical reactions including for catalysis, grafting and polymerization. Other uses include for electronics and biomedical applications. Also see the "Use of the Invention" chapter herein. In general by the methods of the invention one may selectively vary the chemical functionality of the above reagents and these inventive reagents are highly useful as performance-enhancing additives to conventional and other plastics.

What is claimed is:

1. A method for the functionalization of polycyclic silicones (PS) comprising, contacting a solution of formula 3 of:

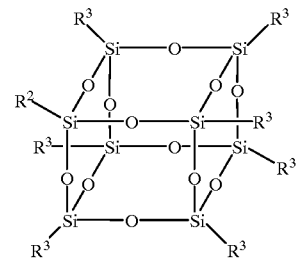

with effective amounts of olefins of alkyls, cyclics, aryls, siloxys or isomers thereof, containing $R^4$ in the presence of effective amounts of a catalyst which promotes oxidative addition to produce a product of formula 4 of:

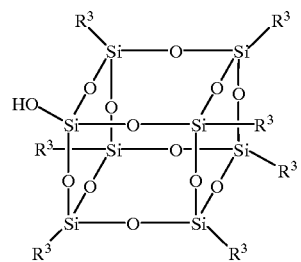

where $R^2$=—Si(CH$_3$)$_2$H (dimethylsilane), —OSi(CH$_3$)$_2$H (dimethylhydridosiloxane), —OSi(CH$_3$)$_2$(CH$_2$)$_n$Si(CH$_3$)$_2$H, —OSi(CH$_3$)$_2$(CH$_2$)$_n$OSi(CH$_3$)$_2$H,
—OSi(CH$_3$)$_2$(OSi(CH$_3$)$_2$O)$_n$Si(CH$_3$)$_2$H, —OSi(CH$_3$)$_2$(CH$_2$)$_n$(C$_6$H$_6$)$_n$(CH$_2$)$_n$Si(CH$_3$)$_2$H, —OSi(CH$_3$)$_2$(CH$_2$)$_n$(C$_6$H$_6$)$_n$Si(CH$_3$)$_2$H,
—OSi(CH$_3$)$_2$(CH$_2$)$_n$(C$_6$H$_6$)$_n$OSi(CH$_3$)$_2$H, —(CH$_2$)$_n$OSi(Me)$_2$H, —O(CH$_2$)$_n$OSi(Me)$_2$H, —O(CH$_2$)$_n$Si(CH$_3$)$_2$H, —(CH$_2$)$_n$(C$_6$H$_5$)$_n$OSi(Me)2H,
—O(CH$_2$)$_n$(C$_6$H$_5$)$_n$OSi(Me)$_2$H, —(CH$_2$)$_n$(C$_6$H$_5$)$_n$Si(Me)$_2$H, —(CH$_2$)$_n$SH (alkylsulfide), —(CH$_2$)$_n$PH$_2$ (alkylphosphine), and —(CH$_2$)$_n$P(R)H (dialkyl-phosphine), and n=1–42, R$^3$ is CH=CH$_2$ (vinyl), —CH$_2$CH=CH$_2$ (allyl), —CH$_2$(CH$_2$)$_n$CH=CH$_2$, ($\alpha$-olefins, n=1–42), —OSi(Me)$_2$CH$_2$(CH$_2$)$_n$CH=CH$_2$ ($\alpha$-olefins, n=1–42)(CH$_2$)$_n$CH=CH(CH$_2$)$_n$CH$_3$ (cis and trans internal olefins, n=1–42), —OSi(Me)$_2$(CH$_2$)$_n$CH=CH(CH$_2$)$_n$CH$_3$ (cis and trans internal olefins, n=1–42), —Si(CH$_3$)$_2$CH=CH$_2$ (dimethylvinylsilane), —Si(CH$_3$)$_2$CH$_2$CH=CH$_2$ (dimethylallylsilane), —OSi(CH$_3$)$_2$CH=CH$_2$ (dimethylvinylsiloxane), —OSi(CH$_3$)$_2$CH$_2$CH=CH$_2$ (dimethylallylsiloxane) and cyclic olefins and hydrocarbon radicals, —CH$_3$ (methyl), —CH$_2$CH$_3$ (ethyl) and their higher analogues —CH$_2$(CH$_2$)$_n$CH$_3$, n=1–42, as well as branched isomers and cyclic isomers cyclo-C$_5$H$_9$ (cyclopentyl), cyclo-C$_6$H$_{11}$ (cyclohexyl) and aromatic analogues —C$_6$H$_5$ (phenyl), and R$^4$=: epoxides, caprolactams, cyclicolefin, $\alpha$-olefins, fluorinated $\alpha$-olefins, mono, di and tri-halides, (including 5-bromo-1-pentene) alcohols, acids, esters, amines, nitriles, cyanates, amides, alcohols, silanols, trihalosilanes, trialkoxysilanes and cis or trans internal olefins.

2. The method of claim 1 wherein said olefins are selected from the group of R$^4$.

3. The method of claim 1 wherein said catalyst is selected from the group of hydrosilation, hydrosulfonation and phosphorylation catalysts.

4. The method of claim 3 wherein from 0.5 to 30% by wt. of said catalyst to said PS is employed at temperatures of 20 to 150° C.

5. The method claim 1 wherein said formula 3 containing at least one hydridosilane (Si—H) substituent is contacted with said olefins in in the presence of a hydrosilylation catalyst to produce compounds of said formula 4.

6. The method of claim 1 wherein said formula 3 containing at least one hydridosiloxane (OSiR$_2$H) substituent, is contacted with said olefins in the presence of a hydrosilylation catalyst to produce compounds of said formula 4.

7. The method of claim 1 wherein said formula 3 containing at least one $\alpha$-olefin substituent, is contacted with silanes (HR$_2$SiR$^4$), in the presence of a hydrosilylation catalyst to produce compounds of said formula 4.

8. The method of claim 1 wherein said formula 3 containing at least one thiol (S—H) substituent, is contacted with said olefins in the presence of a radical catalyst in a hydrosulfonation reaction to produce compounds of said formula 4.

9. The method of claim 1 wherein said formula 3 containing at least one hydridophosphine (P—H) substituent, is contacted with said olefins in the presence of a radical catalyst in a phosphorylation reaction to produce compounds of said formula 4.

10. The method claim 1 wherein said formula 3, in which R$^2$ is selected from the group of alkyl, aryl, halogen, amino and alkoxy, is contacted with water in a hydrolytic cleavage reaction to provide formula 5 with the composition R$_8$T$_8$(OH) or R$_{8-n}$T$_8$(OH)$_n$.

11. The method of claim 1 according to:

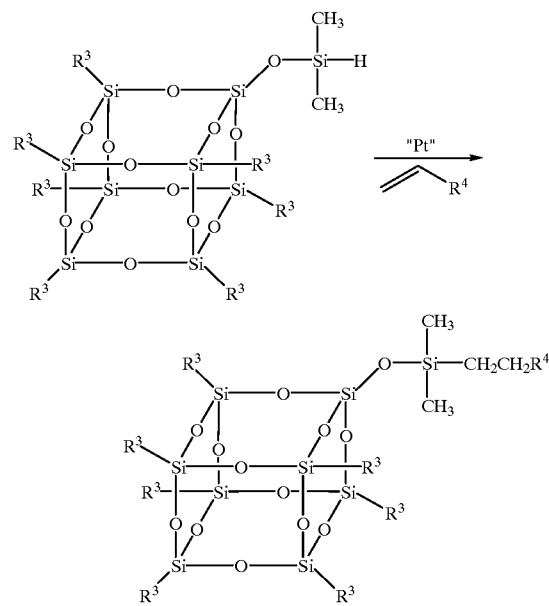

where R$^2$=OSi(CH$_3$)$_2$H (dimethylsiloxane).

12. The method of claim 1 according to:

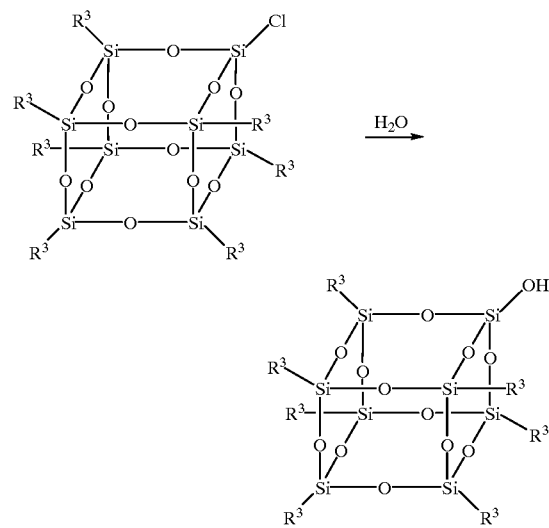

13. The method of claim 1 according to:

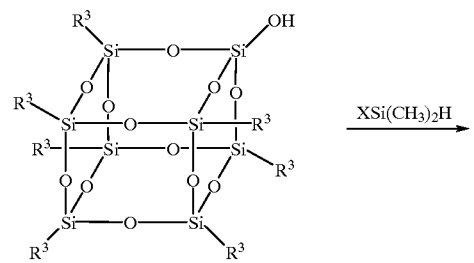

-continued

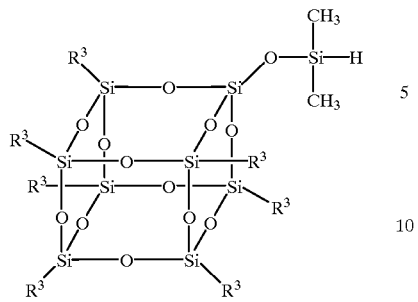

where X=halogen, $NR_2$, or $N(Ph)CON(c-C_4H_8)$.

14. The method of claim 1 wherein the compound of formula 4 is functionalized at the R4 branch for grafting or polymerization thereof.

15. Novel compounds comprising POSS/POS monomers prepared according the method of claim 1 and having at least one reactive functionality.

16. Novel compounds comprising POSS/POS monomers of formula 4 as follows:

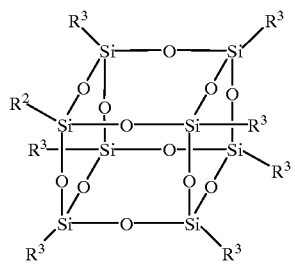

where R2, R3 and R4 are as stated in claim 1.

17. Novel compounds comprising POSS/POS monomers as follows:

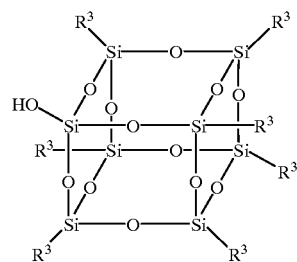

where R2, R3 and R4 are as stated in claim 1.

18. Novel compounds comprising POSS/POS monomers as follows:

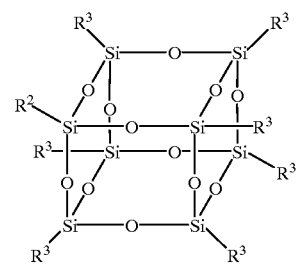

where $R^3$ is as stated in claim 1.

* * * * *